United States Patent
Soma

(10) Patent No.: US 8,883,835 B2
(45) Date of Patent: Nov. 11, 2014

(54) PLANT DISEASE CONTROLLING COMPOSITION AND METHOD FOR CONTROLLING PLANT DISEASE

(75) Inventor: Masato Soma, Narashino (JP)

(73) Assignee: Sumitomo Chemical Company, Limited, Tokyo (JP)

(*) Notice: Subject to any disclaimer, the term of this patent is extended or adjusted under 35 U.S.C. 154(b) by 194 days.

(21) Appl. No.: 12/934,451

(22) PCT Filed: Mar. 24, 2009

(86) PCT No.: PCT/JP2009/056427
§ 371 (c)(1),
(2), (4) Date: Dec. 21, 2010

(87) PCT Pub. No.: WO2009/119873
PCT Pub. Date: Oct. 1, 2009

(65) Prior Publication Data
US 2011/0092556 A1 Apr. 21, 2011

(30) Foreign Application Priority Data
Mar. 25, 2008 (JP) .................... 2008-077975

(51) Int. Cl.
*A01N 43/653* (2006.01)
*A01N 47/16* (2006.01)

(52) U.S. Cl.
CPC ............. *A01N 47/16* (2013.01); *A01N 43/653* (2013.01); *A01N 2300/00* (2013.01)
USPC ........................................ 514/383

(58) Field of Classification Search
CPC .. A01N 47/16; A01N 43/653; A01N 2300/00
USPC ........................................ 514/383
See application file for complete search history.

(56) References Cited

U.S. PATENT DOCUMENTS

| 6,294,567 B1 | 9/2001 | Hashizume et al. | |
| 6,372,787 B1* | 4/2002 | Ziegler et al. | 514/538 |
| 2006/0089315 A1* | 4/2006 | Otsubo et al. | 514/22 |
| 2011/0105489 A1* | 5/2011 | Soma et al. | 514/229.2 |

FOREIGN PATENT DOCUMENTS

| EP | 1 652 429 A1 | 5/2006 | |
| EP | WO 2008/095890 * | 8/2008 | ............. A01N 43/56 |
| WO | WO 98/43480 A1 | 10/1998 | |

OTHER PUBLICATIONS

International Preliminary Report on Patentability (Form PCT/IB/373) and Written Opinion of the International Searching Authority (Form PCT/ISA/237) issued on Sep. 28, 2010 in PCT/JP2009/056427.
International Search Report for PCT/JP2009/056427 mailed Dec. 4, 2009.
Office Action No. 289 for corresponding Colombian Patent Application No. 10-117829, dated Jan. 16, 2013.

* cited by examiner

*Primary Examiner* — Sean Basquill
(74) *Attorney, Agent, or Firm* — Birch, Stewart, Kolasch & Birch, LLP

(57) ABSTRACT

There is provided a plant disease controlling composition comprising at least one compound (A) selected from the group consisting of metconazole, bromuconazole and epoxyconazole, as well as a compound represented by the formula (I): as active ingredients. Also provided is a method for controlling a plant disease, which comprises applying at least one compound (A) selected from the group consisting of metconazole, bromuconazole and epoxyconazole, as well as the compound represented by the formula (I) to a plant, a seed of a plant or a cropland.

8 Claims, No Drawings

PLANT DISEASE CONTROLLING COMPOSITION AND METHOD FOR CONTROLLING PLANT DISEASE

TECHNICAL FIELD

The present invention relates to a plant disease controlling composition and a method for controlling a plant disease.

BACKGROUND ART

Heretofore, for controlling a plant disease, while various plant disease controlling agents have been developed (see e.g. JP 2000-226374 A), a plant disease controlling agent having higher activity is always demanded.

DISCLOSURE OF THE INVENTION

An object of the present invention is to provide a plant disease controlling composition showing high plant disease controlling activity, and a method which can effectively control a plant disease.

Under these circumstances, the present inventors have intensively studied and, as a result, have found that an excellent plant disease controlling effect can be obtained by applying a specific sterol biosynthesis-inhibiting compound and a compound represented by the following formula (I). Thus, the present invention has been completed.

That is, the present invention provides:
(1) A plant disease controlling composition comprising at least one compound (A) selected from the group consisting of metconazole, bromuconazole and epoxyconazole, as well as a compound represented by the formula (I):

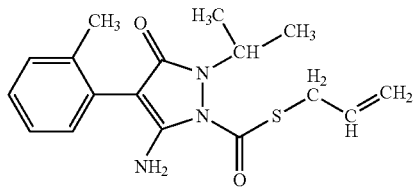

(hereinafter, referred to as the compound I in some cases) as active ingredients (hereinafter, referred to as the present composition);
(2) The plant disease controlling composition according to (1), wherein the compound (A) is metconazole;
(3) The plant disease controlling composition according to (1), wherein the compound (A) is bromuconazole;
(4) The plant disease controlling composition according to (1), wherein the compound (A) is epoxyconazole; and
(5) A method of controlling a plant disease, which comprises applying at least one compound (A) selected from the group consisting of metconazole, bromuconazole and epoxyconazole, as well as a compound represented by the formula (I):

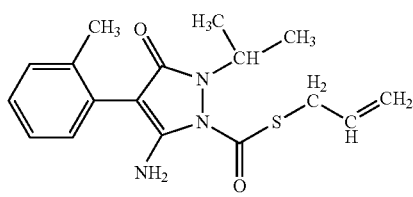

to a plant, a seed of a plant or cropland (hereinafter, referred to as the present controlling method in some cases).

The present composition exhibits high plant disease controlling activity. According to the present controlling method, a plant disease can be effectively controlled.

Hereinafter, in some cases, the term "present invention" refers to both the present composition and the present controlling method.

BEST MODE FOR CARRYING OUT THE INVENTION

In the present invention, the compound I is a known compound and can be synthesized, for example, by the method described in JP 2000-226374 A.

Metconazole, bromuconazole and epoxyconazole exhibit sterol biosynthesis-inhibiting activity, respectively.

Metconazole is described as (1RS,5RS;1RS,5SR)-5-(4-chlorobenzyl)-2,2-dimethyl-1-(1H-1,2,4-triazol-1-ylmethyl)cyclopentanol in pages 689-690 of The Pesticide manual Fourteenth edition.

Bromuconazole is described as 1-[(2RS,4RS:2RS,4SR)-4-bromo-2-(2,4-dichlorophenyl)tetrahydrofurfuryl]-1H-1,2,4-triazole in pages 121-122 of The Pesticide manual Fourteenth edition.

Epoxyconazole is described as (2RS,3SR)-1-[3-(2-chlorophenyl)-2,3-epoxy-2-(4-fluorophenyl)propyl]-1H-1,2,4-triazole in pages 395-396 of The Pesticide manual Fourteenth edition.

Application of these compounds and the compound I exhibits a particularly high plant disease controlling effect because the effect is synergistically exerted.

The present composition may contain, as one or more additional sterol biosynthesis-inhibiting compounds, for example, tetraconazole ((RS)-2-(2,4-dichlorophenyl)-3-(1H-1,2,4-triazol-1-yl)propyl 1,1,2,2-tetrafluoroethyl ether), tebuconazole ((RS)-1-p-chlorophenyl-4,4-dimethyl-3-(1H-1,2,4-triazol-1-ylmethyl)pentan-3-ol), prothioconazole (2-[(2RS)-2-(1-chlorocyclopropyl)-3-(2-chlorophenyl)-2-hydroxypropyl]-2H-1,2,4-triazole-3(4H)-thione), diniconazole ((E)-(RS)-1-(2,4-dichlorophenyl)-4,4-dimethyl-2-(1H-1,2,4-triazol-1-yl)pent-1-en-3-ol), difenoconazole (cis,trans-3-chloro-4-[4-methyl-2-(1H-1,2,4-triazol-1-ylmethyl)-1,3-dioxolan-2-yl]phenyl-4-chlorophenyl ether), myclobutanil (2-p-chlorophenyl-2-(1H-1,2,4-triazol-1-ylmethyl)hexanenitrile), cyproconazole ((2RS,3RS;2RS,3SR)-2-(4-chlorophenyl)-3-cyclopropyl-1-(1H-1,2,4-triazol-1-yl)butan-2-ol), propiconazole ((+−)-1-[2-(2,4-dichlorophenyl)-4-propyl-1,3-dioxolan-2-ylmethyl]-1H-1,2,4-triazole), fenbuconazole (4-(4-chlorophenyl)-2-phenyl-2-(1H-1,2,4-triazol-1-ylmethyl)butyronitrile), hexaconazole ((RS)-2-(2,4-dichlorophenyl)-1-(1H-1,2,4-triazol-1-yl)hexan-2-ol), and penconazole (1-(2,4-dichloro-beta-propylphenethyl)-1H-1,2,4-triazol).

The present invention can be used for farmlands, i.e., cropland, or non-farmlands such as dry field, paddy field, turf and fruit orchard, and can be used for controlling diseases of "crops" such as those listed below without giving phytotoxicity to the crops.

Agricultural crops: corn, rice, wheat, barley, rye, oat, sorghum, cotton, soybean, peanut, buckwheat, sugar beet, rapeseed, sunflower, sugar cane, and tobacco;

Vegetables: Solanaceae vegetables (e.g. eggplant, tomato, green pepper, hot pepper, and potato), Cucurbitaceae vegetables (e.g. cucumber, pumpkin, zucchini, watermelon, and melon), Cruciferae vegetables (e.g. Japanese radish, turnip, horseradish, kohlrabi, Chinese cabbage, cabbage, brown mustard, broccoli, and cauliflower), Compositae vegetables (e.g. burdock, garland chrysanthemum, artichoke, and lettuce), Liliaceae vegetables (e.g. Welsh onion, onion, garlic, and asparagus), Umbelliferae vegetables (e.g. carrot, parsley, celery, and parsnip), Chenopodiaceae vegetables (e.g. spinach, and Swiss chard), Labiatae vegetables (e.g. Japanese basil, mint, and basil), strawberry, sweat potato, yam, and aroid;

Flowers and ornamental plants;

Foliage plant;

Fruit trees: pomaceous fruits (e.g. apple, common pear, Japanese pear, Chinese quince, and quince), stone fleshy fruits (e.g. peach, plum, nectarine, Japanese plum, cherry, apricot, and prune), citrus plants (e.g. Satsuma mandarin, orange, lemon, lime, and grapefruit), nuts (e.g. chestnut, walnut, hazel nut, almond, pistachio, cashew nut, and macadamia nut), berry fruits (e.g. blueberry, cranberry, blackberry, and raspberry), grape, persimmon, olive, loquat, banana, coffee, date, and coconut;

Trees other than fruit trees: tea, mulberry, flowering trees, shrubs, and street trees (e.g. ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, and yew).

The above "crops" include those having herbicide resistance imparted by a classical breeding method, or a genetic engineering technique. Examples of the herbicide to be resisted include an HPPD inhibitor such as isoxaflutole, an ALS inhibitor such as imazethapyr or thifensulfuron-methyl; an EPSP synthesizing enzyme inhibitor; a glutamine synthesizing enzyme inhibitor; and bromoxynil.

Examples of the "crops" having herbicide resistance imparted by a classical breeding method include Clearfield™ canola resistant to an imidazolinone herbicide such as imazethapyr, and STS soybean resistant to a sulfonylurea ALS inhibitor-type herbicide such as thifensulfuron-methyl. Examples of the "crops" having herbicide resistance imparted by a genetic engineering technique include soybean, cotton, and rapeseed cultivars having resistance to glyphosate or glufosinate. Some of such corn cultivars have been already marketed under the trade name of RoundupReady™, and LibertyLink™.

The above "crops" include those having an ability to synthesize, for example, a selective toxin such as that derived from the genus *Bacillus* which ability has been imparted by a genetic engineering technique.

Examples of the toxin expressed by such a genetically modified plant include insecticidal proteins derived from *Bacillus cereus* and *Bacillus popilliae*; δ-endotoxins derived from *Bacillus thuringiensis* such as Cry1Ab, Cry1Ac, Cry1F, Cry1Fa2, Cry2Ab, Cry3A, Cry3Bb1 and Cry9C; insecticidal proteins derived from *Bacillus thuringiensis*, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl syntase; chitinase; and glucanase.

The insecticidal toxin produced by such a genetically modified plant also includes hybrid toxins of 2 or more insecticidal proteins, and toxins in which a part of amino acids constituting an insecticidal protein is deleted or modified. The hybrid toxin is made by a new combination of different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a natural toxin are substituted.

Examples of these toxins and recombinant plants capable of synthesizing these toxins are described, for example, in EP-A-0 374 753, WO 93/07278, WO 95/34656, EP-A-0 427 529, EP-A-451 878, and WO 03/052073.

Toxins contained in these recombinant plants give the plants resistant to, particularly, Coleoptera pests, Diptera pests, or Lepidoptera pests.

In addition, genetically modified plants containing one or plural insecticidal pest-resistant genes and expressing one or plural toxins have been already known, and some of them are commercially available. Examples of these genetically modified plants include YieldGard™ (corn variety expressing Cry1Ab toxin), YieldGard Rootworm™ (corn variety expressing Cry3Bb1 toxin), YieldGard Plus™ (corn variety expressing Cry1Ab and Cry3Bb1 toxins), Herculex I™ (corn variety expressing phosphinothricin N-acetyltransferase (PAT) for imparting resistance to Cry1Fa2 toxin and glufosinate), NuCOTN33B (cotton variety expressing Cry1Ac toxin), Bollgard I™ (cotton variety expressing Cry1Ac toxin), Bollgard II™ (cotton variety expressing Cry1Ac and Cry2Ab toxins), VIPCOT™ (cotton variety expressing VIP toxin), NewLeaf™ (potato variety expressing Cry3A toxin), NatureGard™, Agrisure™ GT Advantage (GA21 glyphosate resistance character), Agrisure™ CB Advantage (Bt11 corn borer (CB) character), and Protecta™.

The above "crops" also include those to which the ability to produce an anti-pathogenic substance having selective activity has been imparted by a genetic engineering technique.

As examples of the anti-pathogenic substance, a PR protein is known (PRPs, EP-A-0 392 225). Such an anti-pathogenic substance and a genetically modified plant producing the same are described, for example, in EP-A-0 392 225, WO 95/33818, and EP-A-0 353 191.

Examples of the anti-pathogenic substance expressed in such the genetically modified plant include ion channel inhibitors such as sodium channel inhibitor, and calcium channel inhibitor (KP1, KP4, KP6 toxins produced by viruses are known); stilbene cynthase; bibenzyl cynthase; chitinase; glucanase; PR protein; anti-pathogenic substances produced by microorganisms such as peptide antibiotics, heterocycle-containing antibiotics, and protein factors involved in plant disease-resistance (described in WO 03/000906).

Examples of plant diseases which can be controlled by the present invention are not limited to, but include the plants and diseases thereof as follows.

Rice: rice blast (*Magnaporthe grisea*), spot leaf blight (*Cochliobolus miyabeanus*), sheath blight (*Rhizoctonia solani*), silly seedling (*Gibberella fujikuroi*);

Wheat, barley, etc.: powdery mildew (*Erysiphe graminis*), red mold (*Fusarium graminearum, F. avenacerum, F. culmorum, Microdochium nivale*), rust (*Puccinia striiformis, P. graminis, P. recondita, P. hordei*), snow mold (*Typhula* sp., *Micronectriella nivalis*), loose smut (*Ustilago tritici, U. nuda*), bunt (*Tilletia caries*), eyespot (*Pseudocercosporella herpotrichoides*), scald disease (Rhynchosporium secalis), leaf blight (*Septoria tritici*), spot blight (*Leptosphaeria nodorum*), net blotch (*Pyrenophora teres* Drechsler);

Citrus fruits: black spot disease (*Diaporthe citri*), scab (*Elsinoe fawcetti*), fruit rot (*Penicillium digitatum, P. italicum*);
Apple: blossom blight (*Monilinia mali*), decomposed disease (*Valsa ceratosperma*), powdery mildew (*Podosphaera leucotricha*), Alternaria blotch (*Alternaria alternata* apple pathotype), scab (*Venturia inaequalis*), anthrax (*Colletotrichum acutatum*), crown rot (*Phytophtora cactorum*);
Pear: scab (*Venturia nashicola, V. pirina*), purple blotch (*Alternaria alternata* Japanese pear pathotype), frogeye (*Gymnosporangium haraeanum*), fruit rot (*Phytophtora cactorum*);
Peach: brown rot (*Monilinia fructicola*), black spot disease (*Cladosporium carpophilum*), Phomopsis rot (*Phomopsis* sp.);
Grape: eastern black disease (*Elsinoe ampelina*), nights grapes rot (*Glomerella cingulata*), powdery mildew (*Uncinula necator*), rust (*Phakqpsora ampelopsidis*), black rot (*Guignardia bidwellii*), downy mildew (*Plasmopara viticola*);
Persimmon: anthracnose (*Gloeosporium kaki*), brown stem rot (*Cercospora kaki, Mycosphaerella nawae*);
Cucurbit: anthracnose (*Colletotrichum lagenarium*), powdery mildew (*Sphaerotheca fuliginea*), vine blight (*Mycosphaerella melonis*), yellow vine disease (*Fusarium oxysporum*), mildew (*Pseudoperonospora cubensis*), Phytophthora rot (*Phytophthora* sp.), seedling damping-off (*Pythium* sp.);
Tomato: ring spot disease (*Alternaria solani*), leaf mold (*Cladosporium fulvum*), late blight (*Phytophthora infestans*);
Eggplant: brown spot disease (*Phomopsis vexans*), powdery mildew (*Erysiphe cichoracearum*);
Cruciferous vegetable: black spot disease (*Alternaria japonica*), vitiligo (*Cercosporella brassicae*), clubroot (*Plasmodiophora brassicae*), mildew (*Peronospora parasitica*);
Leek rust (*Puccinia allii*), soybean purpura (*Cercospora kikuchii*), eastern black disease (*Elsinoe glycines*), black spot disease (*Diaporthe phaseolorum* var. *sojae*), rust (*Phakopsora pachyrhizi*), plaque stalks (*Phytophthora sojae*), bean anthracnose (*Colletotrichum lindemthianum*), peanut black mildew (*Cercospora personata*), brown spot disease (*Cercospora arachidicola*), blight (*Sclerotium rolfsii*);
Pea: powdery mildew (*Erysiphe pisi*);
Potato: early blight (*Alternaria solani*), late blight (*Phytophthora infestans*), powder scab (*Spongospora subterranean f.* sp. *subterranea*);
Strawberry: powdery mildew (*Sphaerotheca humuli*);
Tea: net rice disease (*Exobasidium reticulatum*), disease victory (*Elsinoe leucospila*), ring leaf spot (*Pestalotiopsis* sp.), anthracnose (*Colletotrichum theae-sinensis*);
Tobacco: frogeye (*Alternaria longipes*), powdery mildew (*Erysiphe cichoracearum*), anthracnose (*Colletotrichum tabacum*), mildew (*Peronospora tabacina*), black shank (*Phytophthora nicotianae*);
Sugarbeet: brown spot (*Cercospora beticola*), leaf rot (*Thanatephorus cucumeris*), root rot (*Thanatephorus cucumeris*), black root rot (*Aphanidermatum cochlioides*);
Rose: black spot (*Diplocarpon rosae*), powdery mildew (*Sphaerotheca pannosa*);
Chrysanthemum: brown spot (*Septoria chrysanthemi-indici*), white rust (*Puccinia horiana*);
Diseases caused by the genus *Pythium* of various crops (*Pythium aphanidermatum, Pythium debarianum, Pythium graminicola, Pythium irregulare, Pythium ultimum*), gray mold (*Botrytis cinerea*), white mold, *Sclerotinia* rot, stem rot, crown rot (*Sclerotinia sclerotiorum, Sclerotinia minor*);
Radish: black spot disease (*Alternaria brassicicola*);
Turfgrass: dollar spot disease (*Sclerotinia homeocarpa*), brown patch disease and large patch disease (*Rhizoctonia solani*);
Banana: Sigatoka disease (*Mycosphaerella fijiensis, Mycosphaerella musicola, Pseudocercospora musae*).

The present invention exhibits a particularly high effect on gray mold, white mold, *Sclerotinia* rot, stem rot, crown rot, brown rot, blossom blight, eyespot, and scald disease of various crops, among the above plant diseases.

The weight ratio of the compound (A) and the compound I contained in the present composition is usually 0.125:1 to 20:1, preferably 0.25:1 to 10:1, more preferably 0.25:1 to 1:1 (the compound (A): the compound I).

The present composition may consist in the compound (A) and the compound I without addition of any other ingredients, or may form a formulation in the form of a solid or liquid formulation such as wettable powder, granulated wettable powder, flowable, granules, dry flowable, emulsifiable concentrate, aqueous liquid formulation, oil solution, smoking pesticide, aerosol, and microcapsules.

Usually, these formulations can contain 0.1 to 99% by weight, preferably 0.2 to 90% by weight of the compound (A) and the compound I in total.

These formulations can be prepared, for example, by mixing the compound (A) and the compound I with a solid carrier, a liquid carrier, a gas carrier, and a surfactant and, if necessary, adding auxiliary agents for formulations such as a binder, a dispersant, and a stabilizer.

Examples of the solid carrier include finely divided powders and particles of clays (e.g. kaolin, diatomaceous earth, synthetic hydrous silicon oxide, Fubasami clay, bentonite, or acid clay), talcs, other inorganic minerals (e.g. sericite, quartz powder, sulfur powder, active carbon, calcium carbonate, or hydrated silica). Examples of the liquid carrier include water, alcohols (e.g. methanol, or ethanol), ketones (e.g. acetone, or methyl ethyl ketone), aromatic hydrocarbons (e.g. benzene, toluene, xylene, ethylbenzene, or methylnaphthalene), aliphatic hydrocarbons (e.g. n-hexane, cylcohexanone, or kerosene), esters (e.g. ethyl acetate, or butyl acetate), nitriles (e.g. acetonitrile, or isobutylonitrile), ethers (e.g. dioxane, or diisopropyl ether), acid amides (e.g. dimethylformamide, or dimethylacetamide), and halogenated hydrocarbons (e.g. dichloroethane, trichloroethylene, or carbon tetrachloride).

Examples of the surfactant include alkylsulfates, alkylsulfonates, alkylarylsulfonates, alkyl aryl ethers and polyoxyethylenated compounds thereof, polyoxyethylene glycol ethers, polyhydric alcohol esters, and sugar alcohol derivatives.

Examples of other auxiliary agents for formulations include a binder and a dispersant, specifically, casein, gelatin, polysaccharides (e.g. starch, gum arabic, cellulose derivatives, and alginic acid), lignin derivatives, bentonite, sugars, synthetic water-soluble polymers (e.g. polyvinyl alcohol, polyvinylpyrrolidone, and polyacrylic acids), PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, and fatty acids and esters thereof.

The present composition can also be prepared, for example, by separately formulating the compound (A) and the compound I into different formulations by the above procedures, if necessary, further diluting each of them with water, thereafter, mixing separately prepared different formulations and dilute solutions.

In the present controlling method, respective compounds may be applied to a plant, a seed of a plant or a land where the plant is grown, simultaneously or separately.

In the present controlling method, when the compound (A) and the compound I are simultaneously applied to a plant, a seed of a plant or a cropland, the present composition can be applied, for example, by the following method.

The method of applying the present composition is not particularly limited, as far as the present composition can be substantially applied, and examples thereof include treatment of a plant such as foliage spraying, treatment of a land such as soil treatment, treatment of a seed such as seed disinfection.

While the application amount of the present composition differs depending on various conditions such as a particular content ratio of the compound (A) and the compound I, weather conditions, formulation form, application period, application method, application place, subject disease, and subject crop, the total amount of the compound (A) and the compound I in the soil treatment is usually 1 to 500 g, preferably 2 to 200 g per 1000 m$^2$.

When the present composition is in the form of an emulsifiable concentrate, wettable powder, suspension, or the like, it is usually applied after diluting with water, and the concentration thereof is usually 0.0005 to 2% by weight, preferably 0.005 to 1% by weight of the compound (A) and the compound I in total. When the present composition is in the form of dust, granules or the like, it is usually applied as it is without dilution.

The above application amount in treatment of a seed is in the range of usually 0.001 to 10 g, preferably 0.01 to 1 g of the compound (A) and the compound I in total relative to 1 kg of a seed.

Further, in the present controlling method, when the compound (A) and the compound I are separately applied to a plant, a seed of a plant, or a cropland, both compounds may be separately applied, for example, by the above methods, and the application order of both compounds is not limited. Application methods of both compounds may be the same or different. The interval of applications between both of them is, however, preferably shorter, and desirably within one day.

The application amount of each compound differs depending on various conditions such as a particular application amount ratio of the compound (A) and the compound I, weather conditions, formulation form, application period, application method, application place, subject disease, and subject crop and, the total amount of the compound (A) and the compound I in the soil treatment is usually 1 to 500 g, preferably 2 to 200 g per 1000 m$^2$.

The weight ratio of the compound (A) and the compound I to be applied separately is usually 0.125:1 to 20:1, preferably 0.25:1 to 10:1, further preferably 0.25:1 to 1:1 (the compound (A): the compound I).

When both compounds are in the form of emulsifiable concentrates, wettable powders, suspensions, or the like, the concentration of each compound upon application is usually 0.0005 to 1% by weight, preferably 0.005 to 0.5% by weight, respectively, and when each compound is in the form of dust, granules or the like, it is usually applied as it is without dilution. In treatment of a seed, each of the compound (A) and the compound I is applied in the range of usually 0.001 to 5 g, preferably 0.01 to 0.5 g relative to 1 kg of a seed.

Furthermore, the present composition can be used simultaneously with one or more fungicides, insecticides, miticides, nematocides, herbicides, plant growth regulating agents, fertilizers or soil improvers by mixing with them or without mixing them.

The fungicides, insecticides, miticides, nematocides, herbicides, plant growth regulating agents, fertilizers or soil improvers described above can be the known ones.

Hereinafter, the present invention will be explained in more detail by the following Formulation Examples, Test Examples and Comparative Examples, but the present invention is not limited to them. In the following Examples, all the "parts" are by weight unless otherwise stated. Hereinafter, metconazole, bromuconazole and epoxyconazole are referred to as compound II, compound III and compound IV, respectively, in some cases.

FORMULATION EXAMPLE 1

Three parts of the compound I, 2 parts of any of the compound II to the compound IV, 14 parts of polyoxyethylene styryl phenyl ether, 6 parts of calcium dodecylbenzenesulfonate and 75 parts of xylene are mixed well to prepare each emulsifiable concentrate.

FORMULATION EXAMPLE 2

Five parts of the compound I, 5 parts of any of the compound II to the compound IV, 35 parts of a mixture of white carbon and a polyoxyethylene alkyl ether sulfate ammonium salt (weight ratio 1:1) and 55 parts of water are mixed and pulverized by a wet grinding method to prepare each flowable.

FORMULATION EXAMPLE 3

Twenty parts of the compound I, 2.5 parts of any of the compound II to the compound IV, 1.5 parts of sorbitan trioleate, and 28.5 parts of an aqueous solution containing 2 parts of polyvinyl alcohol are mixed, and pulverized by a wet grinding method, 37.35 parts of an aqueous solution containing 0.05 part of xanthan gum and 0.1 part of aluminum magnesium silicate is added thereto, and 10 parts of propylene glycol is further added thereto, followed by stirring and mixing to prepare each flowable.

FORMULATION EXAMPLE 4

Three parts of the compound I, 2 parts of any of the compound II to the compound IV, 1 part of synthetic hydrous silicon oxide, 2 parts of calcium ligninsulfonate, 30 parts of bentonite and 62 parts of kaolin clay are ground and thoroughly mixed, water is added thereto, and the mixture is thoroughly kneaded, granulated, and dried to prepare each granules.

FORMULATION EXAMPLE 5

Ten parts of the compound I, 40 parts of any of the compound II to the compound IV, 3 parts of calcium ligninsulfonate, 2 parts of sodium laurylsulfate and 45 parts of synthetic hydrous silicon oxide are thoroughly ground and mixed to prepare each wettable powder.

FORMULATION EXAMPLE 6

Two parts of the compound I, 40 parts of any of the compound II to the compound IV, 3 parts of calcium ligninsulfonate, 2 parts of sodium laurylsulfate and 45 parts of synthetic hydrous silicon oxide are thoroughly ground and mixed to prepare each wettable powder.

FORMULATION EXAMPLE 7

Three parts of the compound I, 2 parts of any of the compound II to the compound IV, 85 parts of kaolin clay and 10 parts of talc are thoroughly ground and mixed to prepare each dust.

TEST EXAMPLE 1

A sand loam was filled into a plastic pot, and cucumber (Sagamihanjiro) was seeded, and grown in a greenhouse for 12 days. A flowable of the compound I, and an emulsifiable concentrate of any one of the compound II to the compound IV were diluted with water separately, and they were tank-mixed to prepare a tank mix solution containing the compound I and any one of the compounds II to IV at predetermined concentrations. The tank mix solution was subjected to foliage spraying so that it was sufficiently adhered to a leaf surface of the cucumber. After spraying, the plant was air-dried, and a PDA medium containing hyphae of *Sclerotinia sclerotiorum* was placed on the cucumber leaf surface. After seeding, this was placed under 12° C. and high humidity for 6 days, the controlling effect was investigated.

Separately, for comparison, a flowable of the compound I, or an emulsifiable concentrate of any one compound of the compound II to the compound IV was diluted with water to prepare a water-diluted solution containing the predetermined amount of any one of compounds I to IV, and the similar controlling test was carried out.

Further, for calculating an effective value, an onset area rate (ratio of onset area occupied in leaf area examined) in each treatment group was determined.

The effective value was calculated by the Equation 1.

Effective value(%)=100×(A−B)/A    "Equation 1"

A: Onset area rate of non-treated group
B: Onset area rate of treated group

In general, a effective value expected in treatment by mixing given two kinds of active ingredient compounds, i.e., an expected effective value is calculated by a Colby calculation equation of the Equation 2.

E=X+Y−(X×Y)/100    "Equation 2"

X: Effective value obtained by treatment with M ppm of the compound I
Y: Effective value obtained by treatment with N ppm of the compound II, III or IV
E: Effective value expected in treatment with M ppm of the compound I and N ppm of the compound II, III or IV (expected effective value)

In addition, a synergistic effect was shown herein by a value calculated by the following Equation 3.

Synergistic effect=100×[(actual effective value)/(expected effective value)]    "Equation 3"

The results are shown in Table 1.

TABLE 1

| Test compound | Active ingredient concentration (ppm) | Actual effective value | Expected effective value | Synergistic effect |
|---|---|---|---|---|
| (Compound I) + (Compound II) | 3.1 + 3.1 | 83 | 60 | 138 |
| (Compound I) + (Compound III) | 3.1 + 3.1 | 80 | 59 | 136 |

TABLE 1-continued

| Test compound | Active ingredient concentration (ppm) | Actual effective value | Expected effective value | Synergistic effect |
|---|---|---|---|---|
| (Compound I) + (Compound IV) | 3.1 + 3.1 | 87 | 61 | 143 |
| (Compound I) + (Compound II) | 3.1 + 0.8 | 68 | 58 | 117 |
| (Compound I) | 3.1 | 58 | — | — |
| (Compound II) | 3.1 | 5 | — | — |
| (Compound II) | 0.8 | 0 | — | — |
| (Compound III) | 3.1 | 1 | — | — |
| (Compound IV) | 3.1 | 6 | — | — |

Industrial Applicability

According to the present invention, it is possible to provide a plant disease controlling composition showing the high plant disease controlling activity, and a method by which a plant disease can be effectively controlled.

The invention claimed is:

1. A plant disease controlling composition comprising at least one compound (A) selected from the group consisting of metconazole, bromuconazole and epoxyconazole, as well as a compound represented by the formula (I):

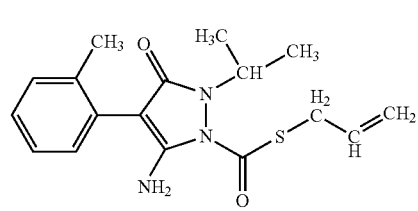

as active ingredients wherein the weight ratio of the compound (A) to the compound represented by the formula (I) is in the range of 0.125:1 to 20:1.

2. The plant disease controlling composition according to claim 1, wherein the compound (A) is metconazole.

3. The plant disease controlling composition according to claim 1, wherein the compound (A) is bromuconazole.

4. The plant disease controlling composition according to claim 1, wherein the compound (A) is epoxyconazole.

5. A method for controlling a plant disease, Which comprises applying at least one compound (A) selected from the group consisting of metconazoic, bromuconazole and epoxyconazole, as well as a compound represented by the formula (I):

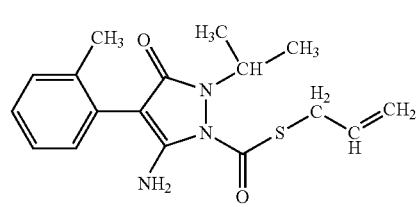

to a plant, a seed of a plant or a cropland.

6. The plant disease controlling composition according to claim 1, wherein the weight ratio of the compound (A) to the compound represented by the formula (I) is in the range of 0.25:1 to 10:1.

7. The plant disease controlling composition according to claim 1, wherein the weight ratio of the compound (A) to the compound represented by the formula (I) is in the range of 0.25:1 to 1:1.

8. The plant disease controlling composition according to claim 2, wherein The weight ratio of the coumpound (A) to the compound represented by the formula (I) is in the range of 0.25:1 to 1:1.

* * * * *